United States Patent
Richardson

(10) Patent No.: US 11,254,085 B2
(45) Date of Patent: Feb. 22, 2022

(54) ABSORBENT MICROSTRUCTURE ARRAYS AND METHODS OF USE

(71) Applicant: Imagine TF, LLC, Campbell, CA (US)

(72) Inventor: Brian Edward Richardson, Los Gatos, CA (US)

(73) Assignee: Imagine TF, LLC, Campbell, CA (US)

( * ) Notice: Subject to any disclaimer, the term of this patent is extended or adjusted under 35 U.S.C. 154(b) by 0 days.

(21) Appl. No.: 16/600,522

(22) Filed: Oct. 13, 2019

(65) Prior Publication Data

US 2020/0039175 A1 Feb. 6, 2020

Related U.S. Application Data

(63) Continuation of application No. 15/233,701, filed on Aug. 10, 2016, now Pat. No. 10,479,046.

(60) Provisional application No. 62/283,051, filed on Aug. 19, 2015.

(51) Int. Cl.
  *B32B 3/08* (2006.01)
  *A61F 13/15* (2006.01)

(52) U.S. Cl.
  CPC ........ *B32B 3/085* (2013.01); *A61F 13/15203* (2013.01); *A61F 2013/15536* (2013.01); *B32B 2307/726* (2013.01); *B32B 2555/02* (2013.01)

(58) Field of Classification Search
  CPC .............. C02F 1/4698; A61F 13/15203; A61F 2013/15536; B32B 3/085; B32B 2307/726; B32B 2555/02; B33Y 80/00
  USPC ........................................................ 210/747.6
  See application file for complete search history.

(56) References Cited

U.S. PATENT DOCUMENTS

| | | | | |
|---|---|---|---|---|
| 4,410,427 A | * | 10/1983 | Wydeven | B01D 46/12 210/317 |
| 8,357,219 B2 | * | 1/2013 | Boehrs | F02M 35/02416 55/480 |
| 2003/0104170 A1 | * | 6/2003 | Johnston | B01D 1/00 428/167 |
| 2006/0163150 A1 | * | 7/2006 | Golden | B01D 25/24 210/493.1 |
| 2014/0224658 A1 | * | 8/2014 | Richardson | B01D 46/40 204/630 |
| 2015/0336360 A1 | * | 11/2015 | Bhushan | B08B 17/065 428/195.1 |

* cited by examiner

*Primary Examiner* — Frank J Vineis
*Assistant Examiner* — Laura B Figg
(74) *Attorney, Agent, or Firm* — Keith Kline; The Kline Law Firm PC

(57) ABSTRACT

Absorbent microstructure panels are described herein. An example filter device includes a plurality of microstructure panels each having a front surface and a back surface, and a plurality of capillary ridges protruding from the front surface. The plurality of capillary ridges are each spaced apart from one another. The plurality of microstructure panels form an absorbent microstructure array by layering the plurality of microstructure panels together such that the plurality of capillary ridges of one microstructure panel contacts the back surface of an adjacent microstructure panel to create capillary tubes that draw fluid into the absorbent microstructure array.

13 Claims, 16 Drawing Sheets

ABSORBENT MICROSTRUCTURE ARRAYS AND METHODS OF USE

CROSS REFERENCE TO RELATED APPLICATIONS

This application claims the priority benefit of U.S. Provisional Application 62/283,051, filed on Aug. 19, 2015, and is a continuation application of U.S. application Ser. No. 15/233,701, filed on Aug. 10, 2016, the disclosures of which are hereby incorporated by reference in their entirety, including all references and appendices cited therein.

FIELD OF TECHNOLOGY

The present disclosure is generally directed to absorbent objects, and more particularly, but not by way of limitation, to absorbent microstructure arrays that are comprised of a plurality of microstructure panels having capillary features. The plurality of microstructure panels when stacked together form capillary tubes that draw fluid into the absorbent microstructure array.

SUMMARY

Generally, the present disclosure is directed to absorbent microstructure arrays that are used to absorb a fluid.

According to some embodiments, the present disclosure is directed to an absorbent microstructure array, comprising: (a) a plurality of microstructure panels each having: (i) a front surface, a back surface, an upper edge, and a lower edge; (ii) a plurality of capillary ridges protruding from the front surface, the plurality of capillary ridges being spaced apart from one another; and (b) a plurality of microstructure panels that form an absorbent microstructure array by layering the plurality of microstructure panels together such that the plurality of capillary ridges of one microstructure panel contacts the back surface of an adjacent microstructure panel to create capillary tubes that draw fluid into the absorbent microstructure array.

According to some embodiments, the present disclosure is directed to an absorbent microstructure array, comprising: (a) a plurality of microstructure panels each having: (i) a front surface, a back surface, an upper edge, and a lower edge; and (ii) a corrugated capillary profile associated with the front surface, the corrugated capillary profile comprising alternating capillary ridges and capillary channels, the capillary ridges forming a first set of capillary tubes with the front surface; and (b) a plurality of microstructure panels that form an absorbent microstructure array by layering the plurality of microstructure panels together such that the capillary ridges of one microstructure panel contact the back surface of an adjacent microstructure panel to create a second set of capillary tubes from the capillary channels.

According to some embodiments, the present disclosure is directed to a flexible absorbent microstructure array, comprising: (a) a plurality of flexible microstructure panels each having: (i) a front surface and a back surface; and (ii) a plurality of capillary ridges protruding from the front surface, the plurality of capillary ridges being spaced apart from one another; and (b) a plurality of microstructure panels that form an absorbent microstructure array by layering the plurality of microstructure panels together such that the plurality of capillary ridges of one microstructure panel contacts the back surface of an adjacent microstructure panel to create capillary tubes that draw fluid into the absorbent microstructure array.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

The present disclosure is directed to absorbent microstructure arrays that can be utilized in a wide variety of products. Examples of products that can incorporate the absorbent microstructure arrays include, but are not limited to diapers, mops, hygiene, sponges, and towels—just to name a few.

The absorbent microstructure arrays can be fabricated with flexible or ridged materials. In the case of a sponge, where it is desirable to squeeze out fluids from the capillary tubes, portions of the absorbent microstructure arrays should be flexible. In the case of a diaper, portions of the absorbent microstructure arrays are ridged so the fluid is not expelled when an individual moves or sits while other portions of the absorbent microstructure arrays are flexible to allow for the diaper to conform to the body.

In some embodiments, the absorbent microstructure arrays can be utilized to uptake and store a fluid. The absorbent microstructure arrays can be used to transport the fluid in one or more embodiments.

Figure 1:
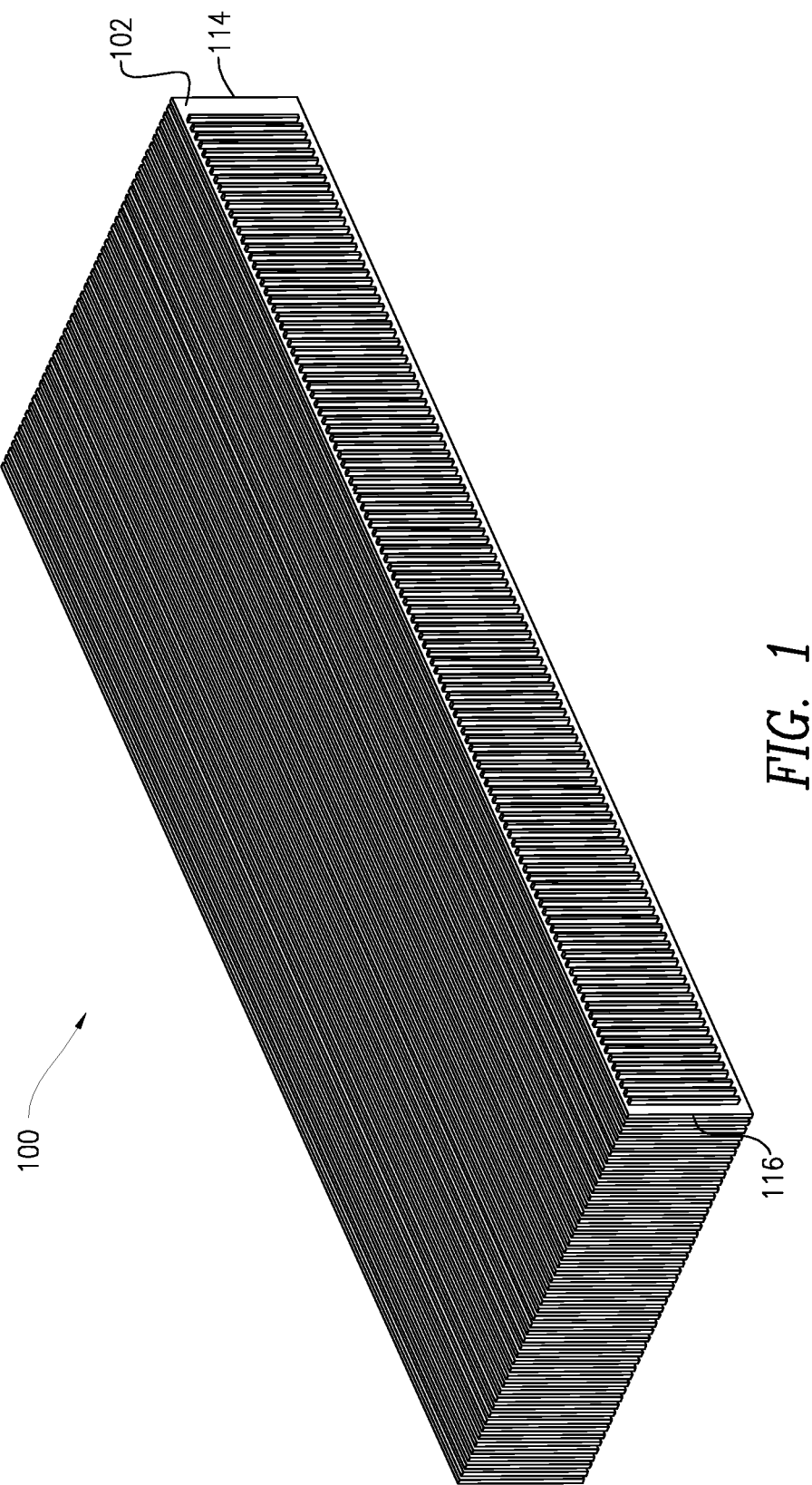
FIG. 1 is a perspective view of an example absorbent microstructure array of the present disclosure.

FIG. 1 illustrates an embodiment of an example absorbent microstructure array (referred to hereinafter as "array 100") that is comprised of a plurality of microstructure panels, such as microstructure panel 102. The plurality of microstructure panels are layered or stacked in various configurations to create the array 100. For reference, the array 100 can have a height of approximately one millimeter in one embodiment. Absorbent microstructure arrays can have any dimension desired, based on design requirements such as volume of fluid to be absorbed and a size of an object that is to incorporate the absorbent microstructure array(s).

Figure 2:
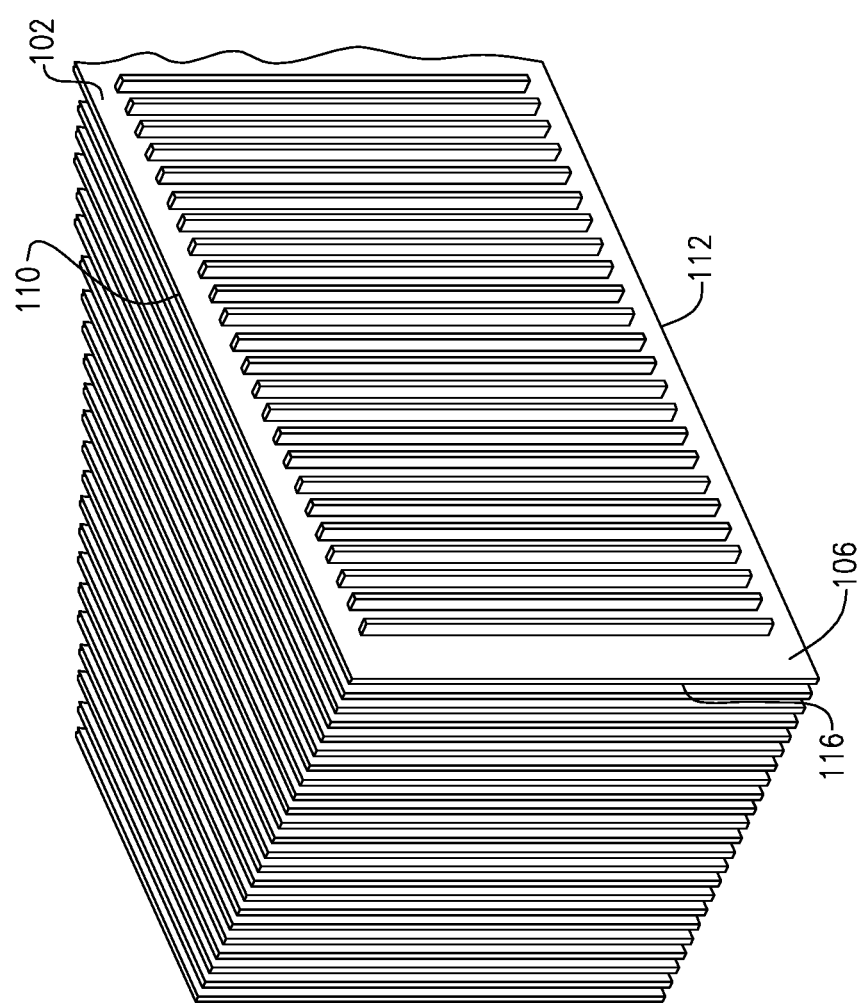
FIG. 2 is a close up perspective view of the example absorbent microstructure array of FIG. 1.
Figure 3:
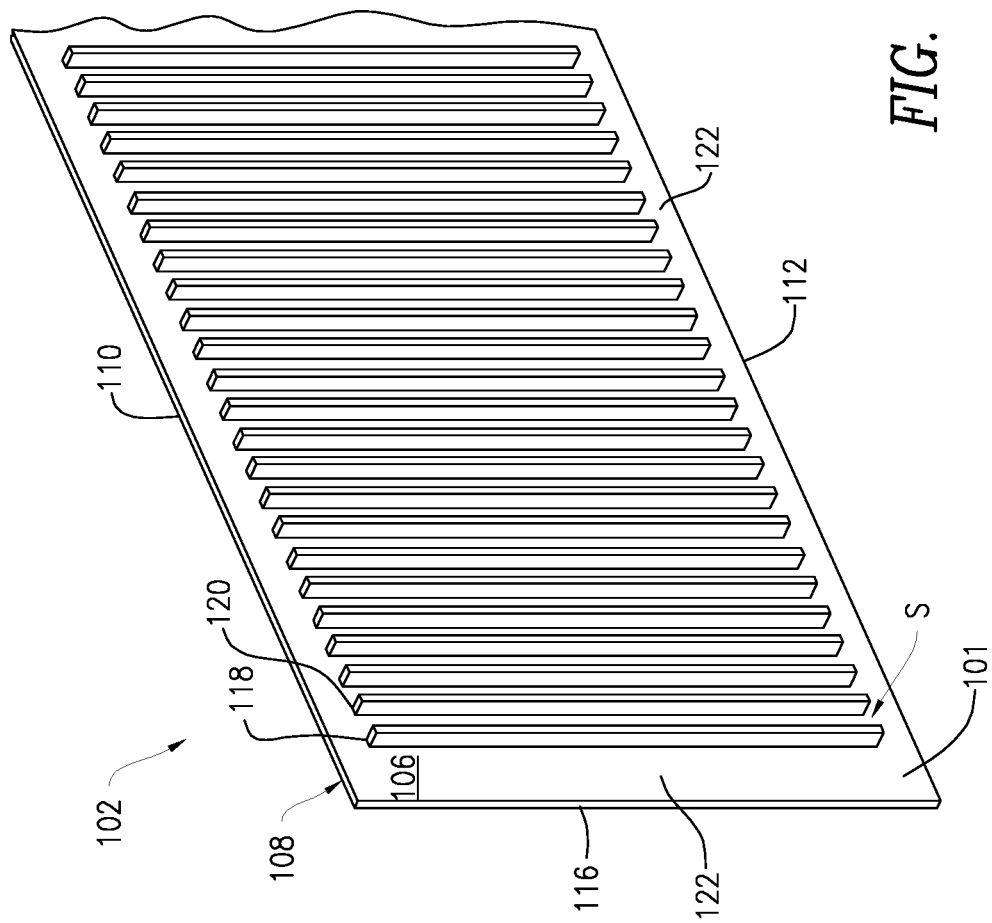
FIG. 3 is a perspective view of an example microstructure panel of the absorbent microstructure array of FIG. 1.

FIGS. 2 and 3 collectively illustrate a close-up perspective view of the microstructure panel 102 that comprises a front surface 106, a back surface 108, an upper edge 110, a lower edge 112, a right edge 114, and a left edge 116. The right edge 114 and left edge 116 are best illustrated in FIG. 1. In some embodiments, the microstructure panel 102 is constructed from a base or substrate 101 that is constructed from a solid material such as a polymer, while in other embodiments the substrate 101 can be fabricated from a porous material that allows fluid to be filtered and or transmitted between the pluralities of microstructure panels.

In one embodiment, the microstructure panel 102 comprises a plurality of capillary ridges, such as capillary ridges 118 and 120, which are adjacent to one another. The capillary ridges protrude or extend from the front surface 106. In one embodiment, a spacing S between the capillary ridges 118 and 120 defines a width dimension of a capillary tube that is created when the microstructure panels are mated together to form the array 100.

The dimensions of an example capillary tube are illustrated below and described in greater detail with reference to FIG. 4.

Each of the capillary ridges extends from the upper edge 110 towards the lower edge 112. In some embodiments, the capillary ridges begin a specified distance from the upper edge 110 and terminate at a distance away from the lower edge 112 to create a border 122 around the plurality of capillary ridges. The leftmost and rightmost ones of the capillary ridges can also be set in at a distance away from the right edge 114 and left edge 116 respectively, to further define the border 122. In some embodiments the microstructure panel does not incorporate a border.

Figure 4:
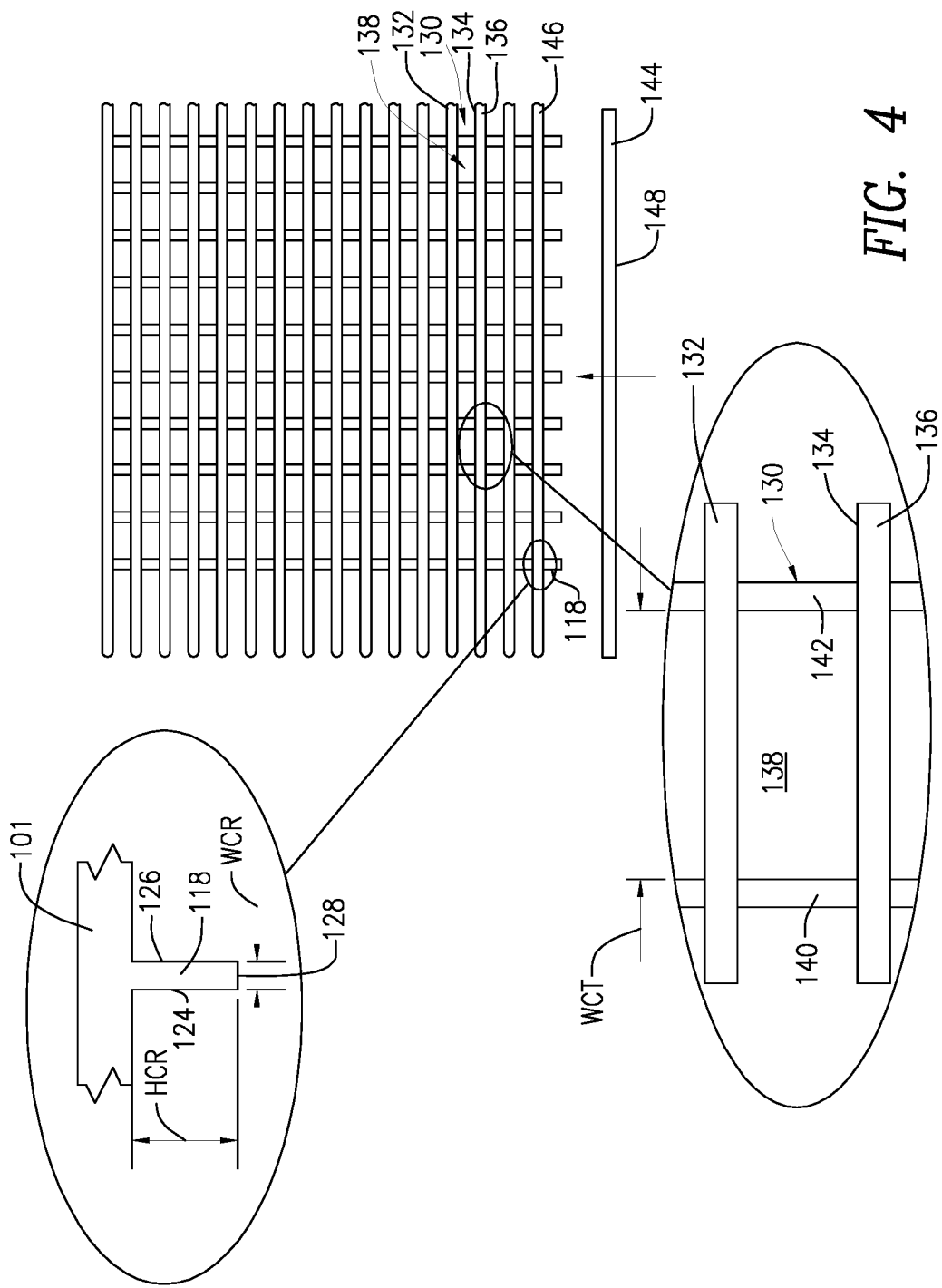
FIG. 4 is a top down perspective view of a portion of the absorbent microstructure array of FIG. 1.

In FIG. 4, the capillary ridges, such as capillary ridge 118 comprises a height HCR that specifies a distance that the capillary ridge 118 extends away from the front surface 106. The capillary ridge 118 also has a width dimension $W_{CR}$ that specifies a distance between opposing sidewalls 124 and 126 of the capillary ridge 118. The capillary ridge 118 also comprises a contacting surface 128 that mates with the back surface of an adjacent panel.

It will be understood that the plurality of microstructure panels form the array 100 by layering the plurality of microstructure panels together such that the plurality of capillary ridges of one microstructure panel contacts the back surface of an adjacent microstructure panel to create capillary tubes that draw fluid into the absorbent microstructure array. For example, the capillary ridges 130 of microstructure panel 132 contact a back surface 134 of an adjacent microstructure panel 136.

In some embodiments, the capillary ridges contact adjacent panels to create capillary tubes, such as capillary tube 138. The capillary tube 138 has a width dimension $W_{CT}$. The width dimension of the capillary tube 138 is defined by the spacing between the capillary ridges, such as capillary ridges 140 and 142. The capillary tube 138 has a substantially rectangular cross section in this embodiment. The shape of the capillary tube 138 is defined by the shape of the sidewalls of the capillary ridges that form a portion of the capillary tube 138. For example, if the sidewalls of the capillary ridges 140 and 142 were concave in shape (measured from the contacting surface of the capillary ridge down to the front surface of the microstructure panel), the capillary tube 138 would have a substantially elliptical cross section.

In some embodiments, an enclosing microstructure panel 144 is placed over the plurality of capillary ridges of a terminal microstructure panel 146 (also referred to in FIGS. 1-3 as microstructure panel 102) of the plurality of microstructure panels. The enclosing microstructure panel has a flat front surface 148 in some embodiments.

Figure 5:
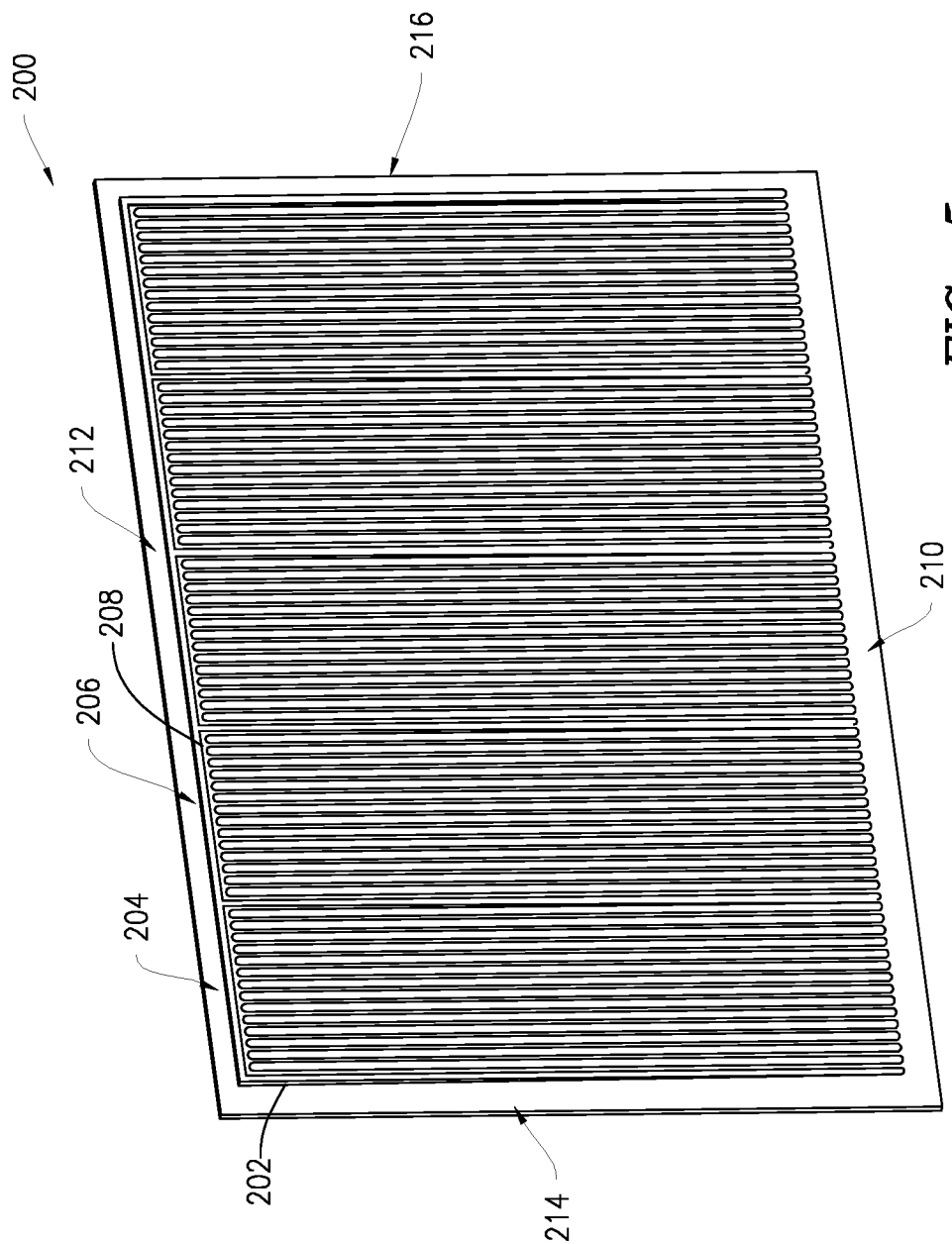
FIG. 5 is a perspective view of another example microstructure panel comprising capillary ridge walls.

FIG. 5 illustrates another microstructure panel 200 that comprises various capillary wall ridges, such as capillary wall ridge 202 that function to restrict fluid flow. In one embodiment, sections of capillary ridges can be separated or segmented using capillary wall ridges. For example a first section capillary ridges 204 is partially surrounded by a capillary wall ridge 202. The first section capillary ridges 204 is disposed adjacent to a second section of capillary ridges 206 that are partially surrounded by a capillary wall ridge 208. Of note, a lower area 210 of the capillary ridges is not enclosed by a capillary wall ridge. Thus, fluid can be drawn between the capillary ridges (when the microstructure panel 200 is assembled into an array) from a lower edge of the microstructure panel 200 but excluded from exiting a top edge 212 of the microstructure panel 200 and/or the right side 214 and left side 216 of the microstructure panel 200. In one use case, when the microstructure panel 200 is made from a flexible material and the microstructure panel 200 compressed, the capillary wall ridges reduce the ability of the fluid to be squeezed from the top or sides of an array.

Figure 6:
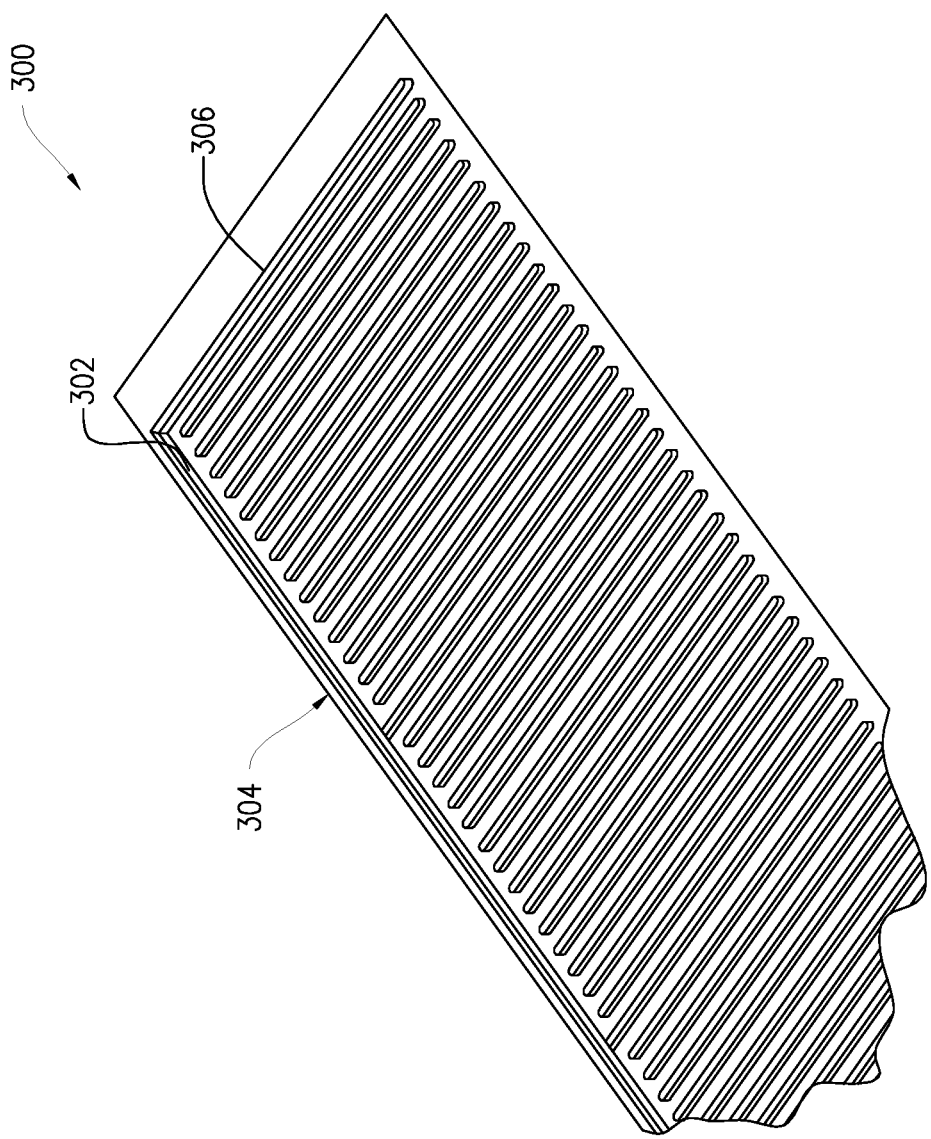
FIG. 6 is a perspective view of an additional example microstructure panel comprising capillary ridge walls.

In FIG. 6, another microstructure panel 300 comprises a capillary wall ridge 302 that extends along a length of an upper edge 304 of the microstructure panel 300 and connects to outermost capillary ridges (such as outermost capillary ridge 306) to prevent fluid from being drawn above the capillary wall ridge or outwardly from a left edge or right edge of the plurality of microstructure panels and/or array when assembled into an absorbent microstructure array.

In addition to varying the construction of the microstructure panels, some embodiments of absorbent microstructure arrays can be layered in unique manners. For example, in FIG. 7, each of a plurality of microstructure panels is laid in a feathered or offset pattern to create an absorbent microstructure array 700. In this configuration, adjacent microstructure panels such as panel 702 and 704 are set at an angle θ that is measured relative to a reference plane P. For context, the reference plane P is oriented perpendicularly to embodiments where the microstructure panels are vertically oriented such as illustrated in FIGS. 1 and 2. In one embodiment, the microstructure panels of the absorbent microstructure array 700 are set at approximately 45 degrees (other angles can likewise be utilized). The angling of the microstructure panels allows for the placement and use of the absorbent microstructure array 700 in a location where height is a limiting factor, such as thin materials like diapers or floor mop heads.

Figure 7:
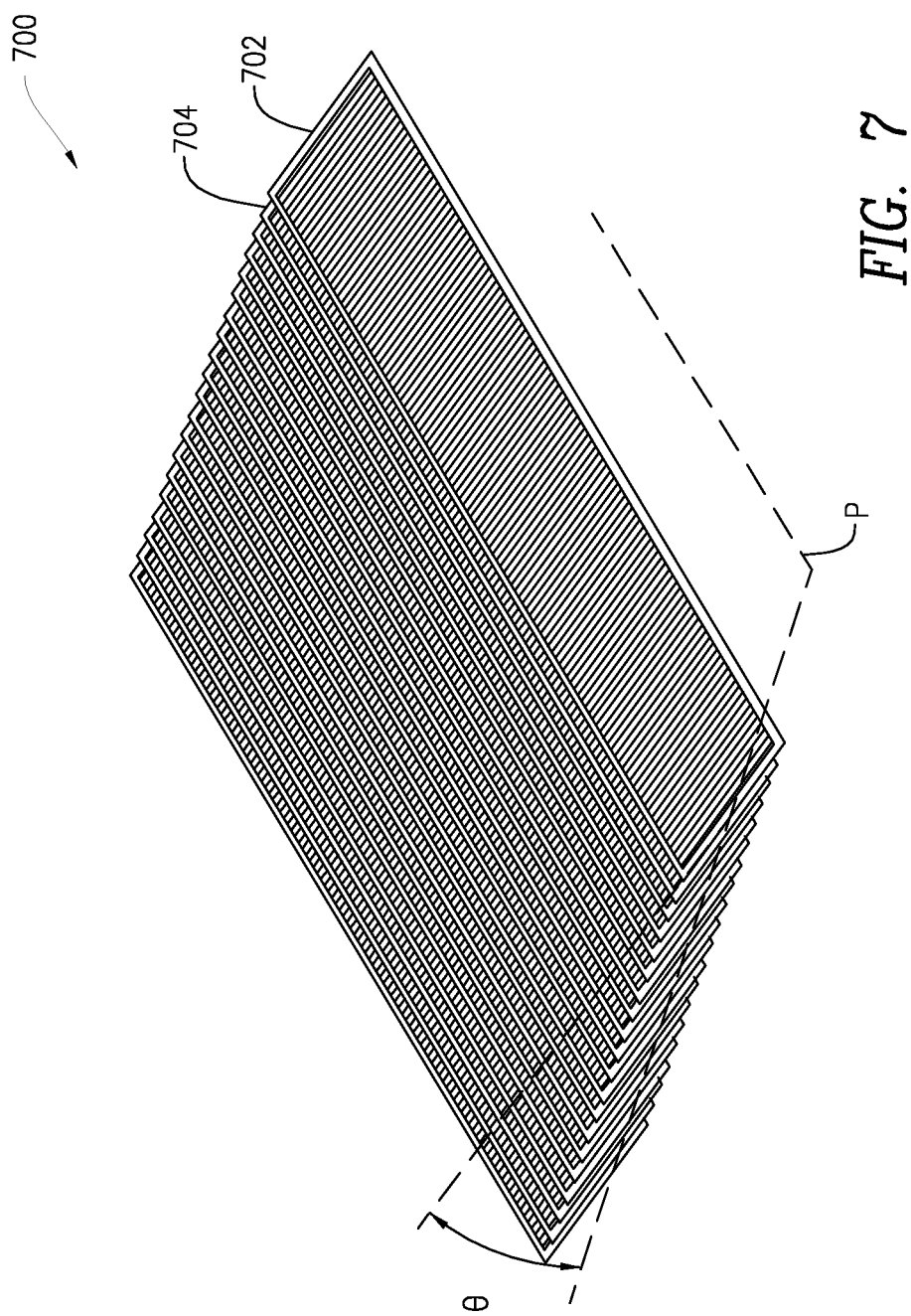
FIG. 7 is a perspective view of another example absorbent microstructure array having microstructure panels set at an angle.
Figure 8:
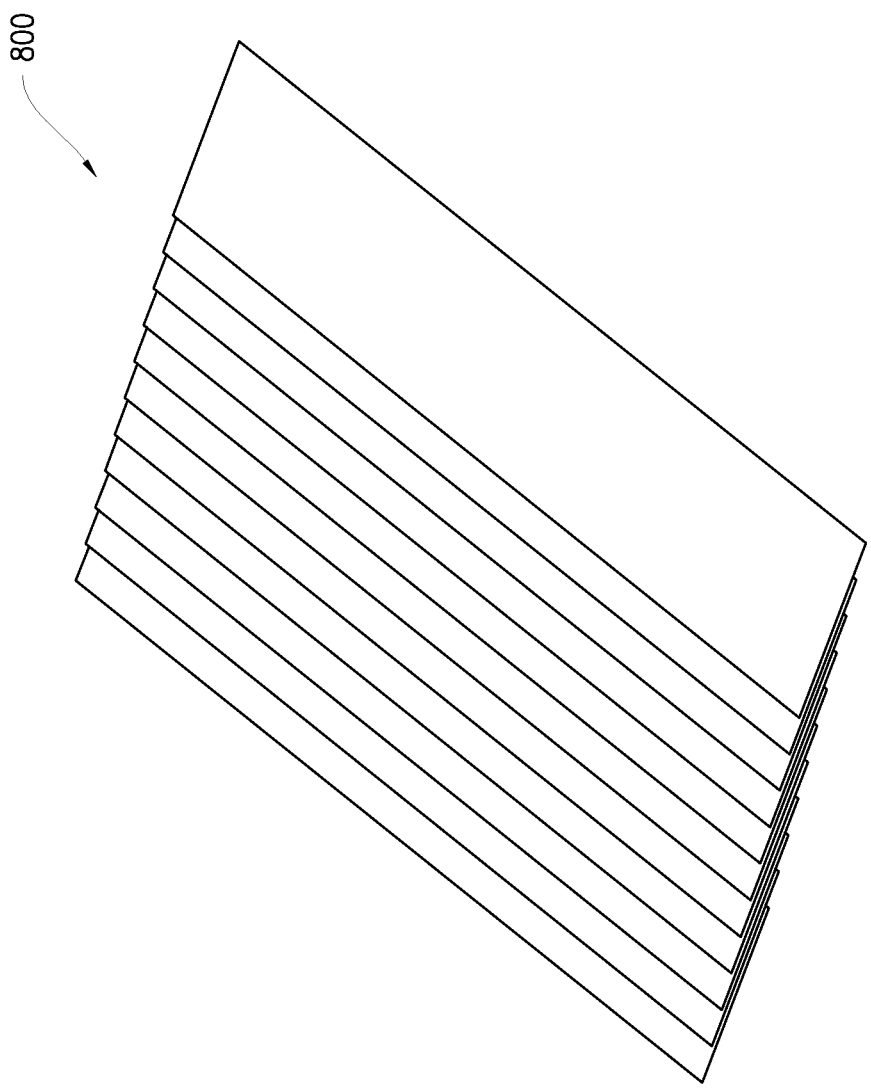
FIG. 8 is a perspective view of an example of an enclosing microstructure panel.

FIG. 8 illustrates an example layer of enclosing microstructure panels 800 that can be placed over exposed ones of the plurality of capillary ridges of the plurality of microstructure panels of the absorbent microstructure array 700 of FIG. 7. In some embodiments, the layer of enclosing microstructure panels 800 each has a flat front surface.

Figure 9:
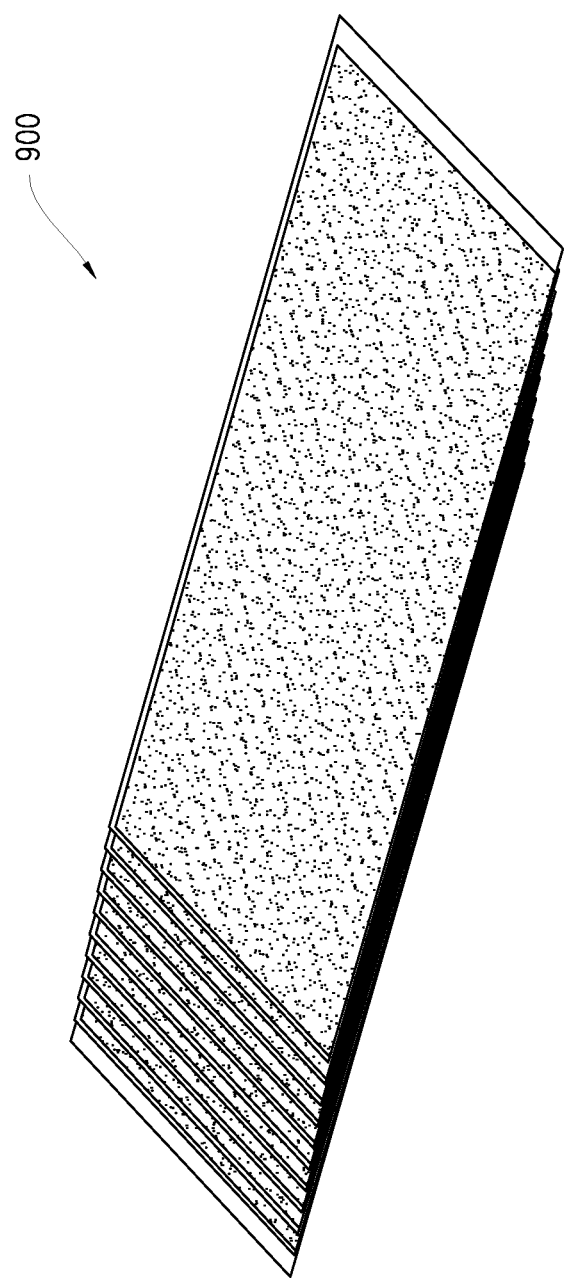
FIG. 9 is a perspective view of an example of an absorbent microstructure array a substantially flat configuration.

FIG. 9 illustrates an example array 900 of microstructure panels that are stacked upon one another in an offset manner. This is a collapsed configuration of microstructure panels which allows the array 900 to be laid relatively flat compared to the angled configuration illustrated in FIG. 8. This configuration of microstructure panels allows for an absorbent array that can be oriented while storing and transporting fluid a significant distance from a collection area.

Figure 10:
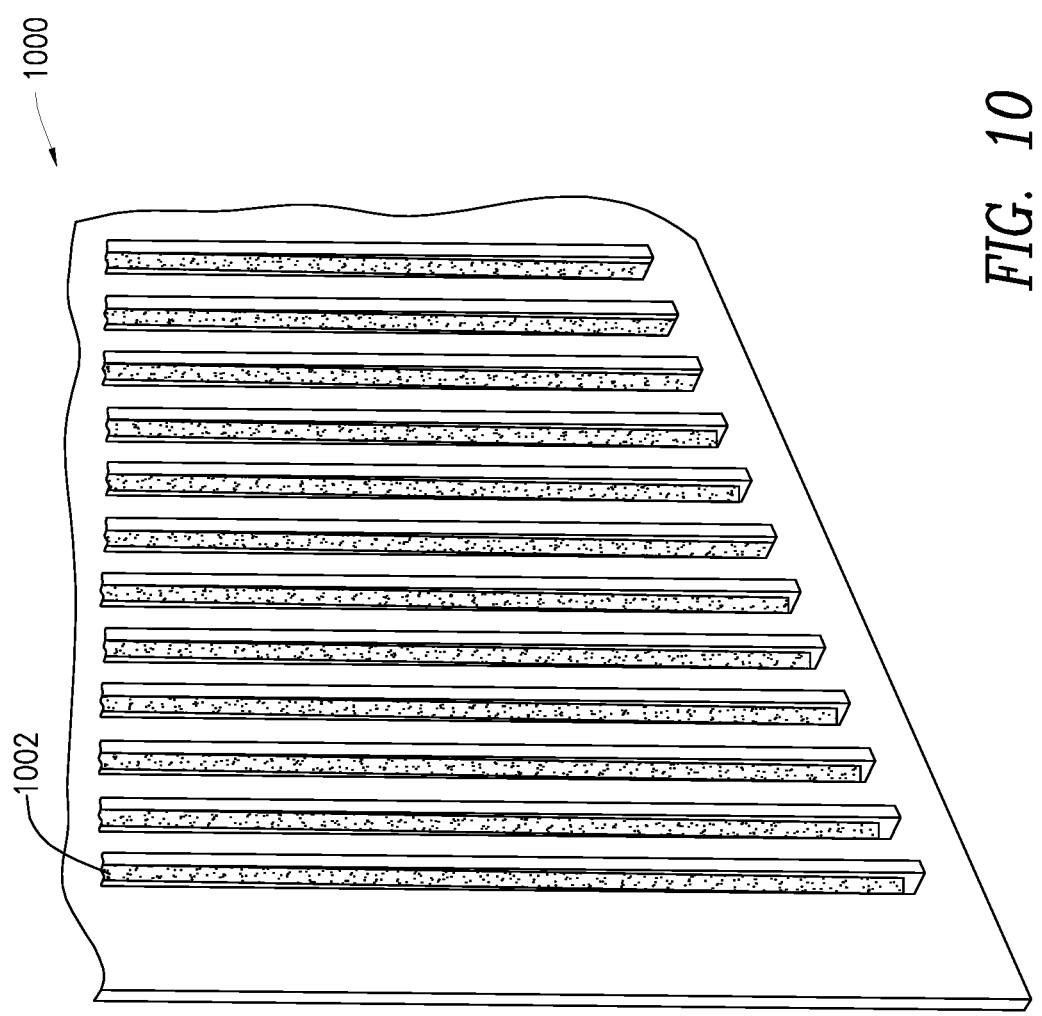
FIG. 10 is a perspective view of an example microstructure panel comprising capillary ridges with a nano-structure coating.

FIG. 10 illustrates another example microstructure panel 1000 that comprises capillary ridges with nano-coating 1002 that function to increase the capillary action of the capillary tubes created when a plurality of the microstructure panels 1000 are joined together to create an absorbent microstructure array. In some embodiments, the nano-coating 1002 includes nano-structures such as bumps that enhance capillary action of the plurality of microstructure panels relative to the plurality of microstructure panels with no nano-structure coating. In FIG. 10, only two of the capillary channel surfaces are shown to be coated. Any number of the surfaces could be coated if desired.

Figure 11:
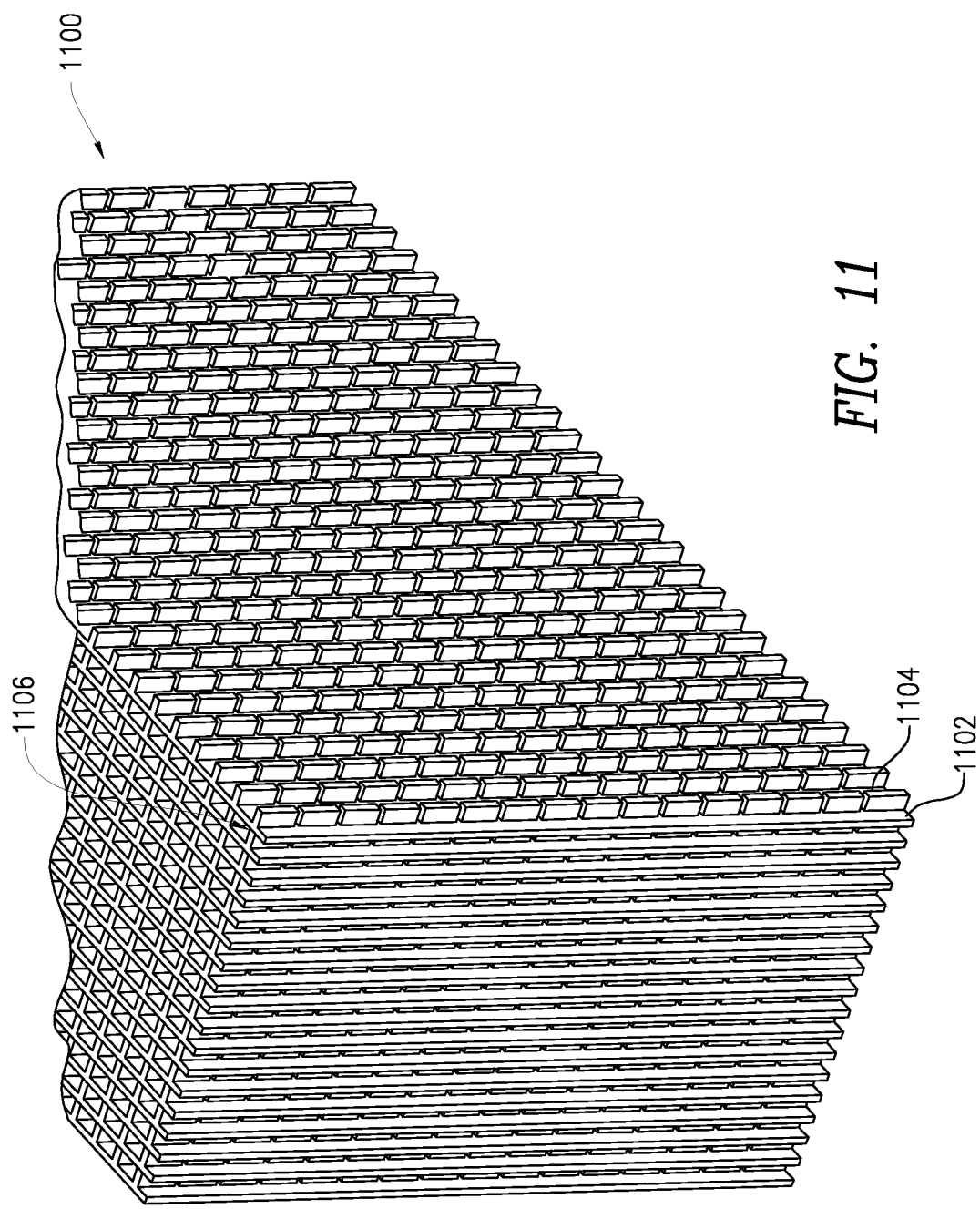
FIG. 11 is a perspective view of an example of an absorbent microstructure array having cross notched capillary ridges.

FIG. 11 illustrates another example absorbent microstructure array 1100 having a plurality of microstructure panels such as microstructure panel 1102 that comprises capillary ridges that have cross-cut notches, such as cross-cut notch 1104. The cross-cut notches create additional volume for fluid collection. That is, when fluid is drawn into a capillary tube 1106, the fluid will begin to cross the capillary ridges through the cross-cut notches.

Figure 12:
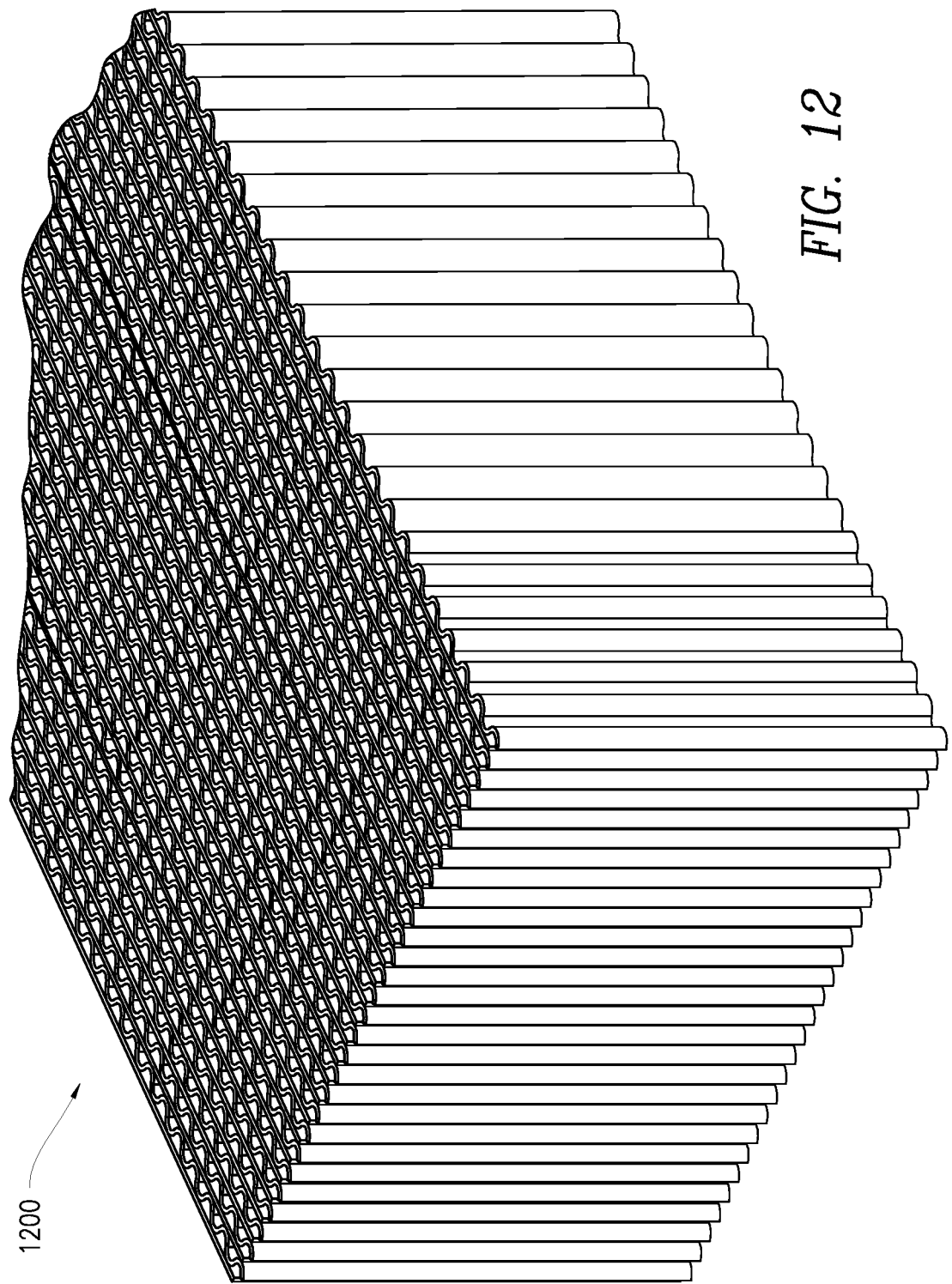
FIGS. 12 and 13 collectively illustrate a perspective view of an example of an absorbent microstructure having microstructure panels with a corrugated capillary profile.
Figure 13:
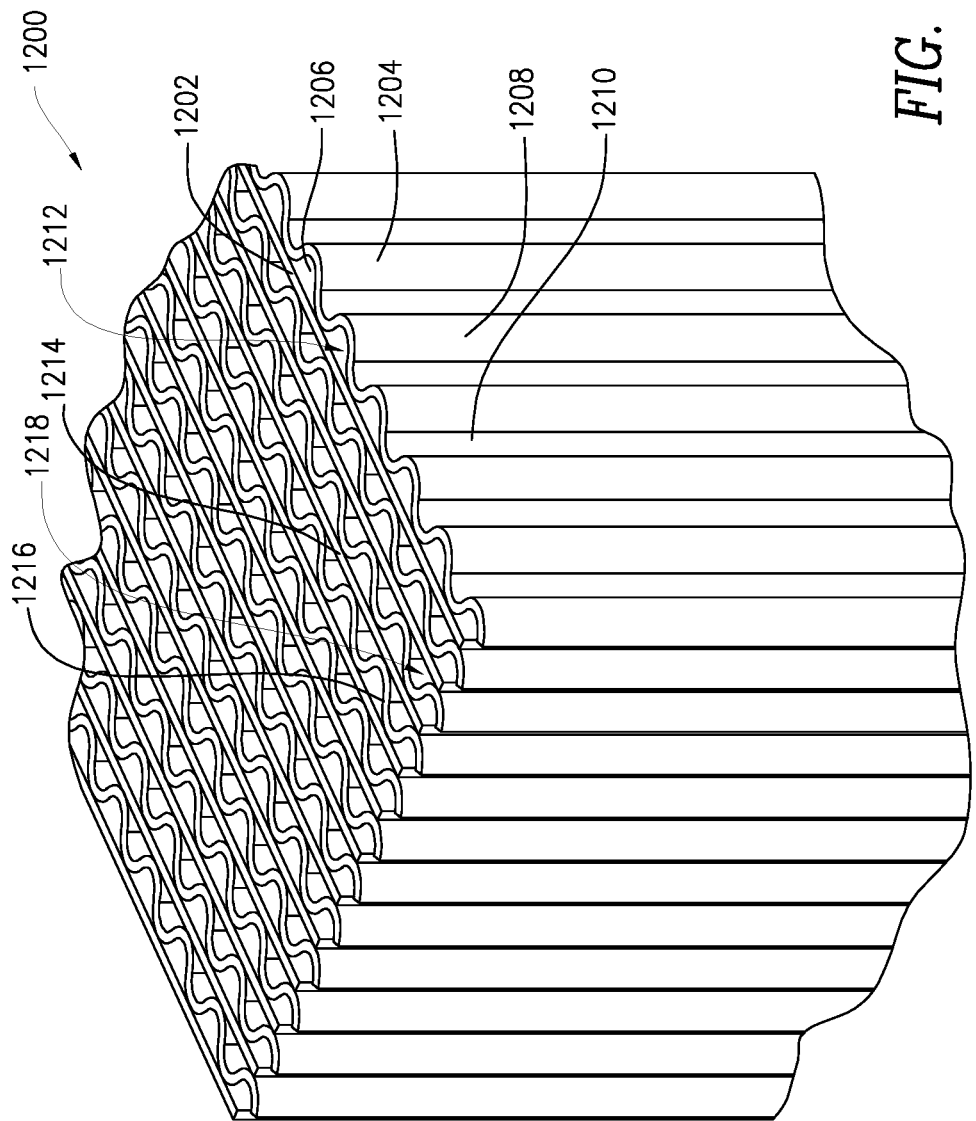

FIGS. 12 and 13 collectively illustrate another example absorbent microstructure array 1200 having microstructure panels with corrugated capillary ridges. For example, the microstructure panel 1202 comprises a corrugated capillary profile 1204 associated with a front surface 1206 of the microstructure panel 1202. In one embodiment, the corrugated capillary profile 1204 comprises alternating capillary ridges, such as capillary ridge 1208 and capillary channels such as capillary channel 1210. The capillary ridges form a first set of capillary tubes, such as capillary tube 1212, with the front surface 1206.

The plurality of microstructure panels form the absorbent microstructure array 1200 by layering the plurality of microstructure panels together such that the capillary ridges of one microstructure panel (for example panel 1214) contact the back surface of an adjacent microstructure panel (for example panel 1216) to create a second set of capillary tubes, such as capillary tube 1218, in cooperation with the capillary channels.

Figure 14:
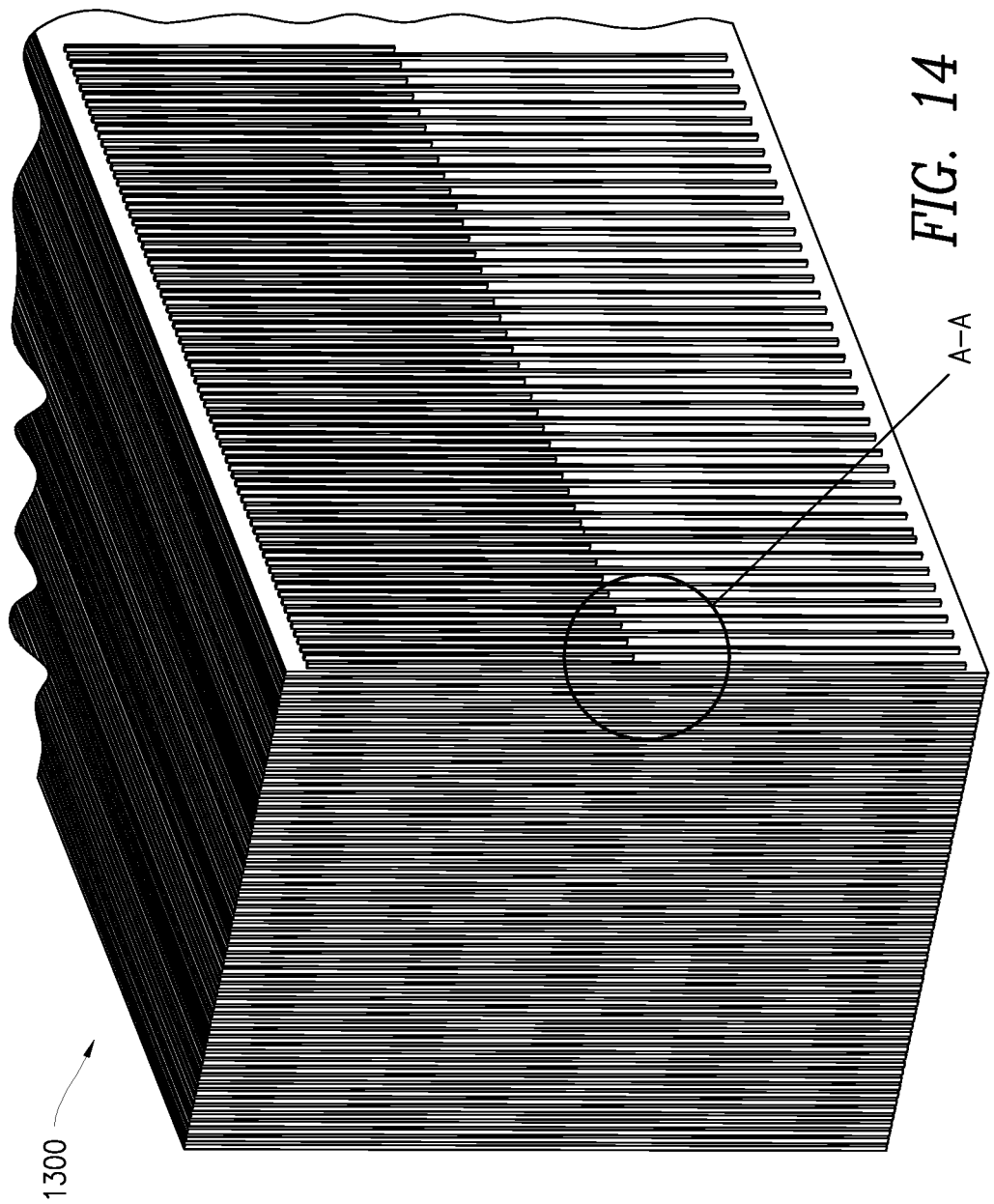
FIG. 14 is a perspective view of an example of an absorbent microstructure array having various rows of differently sized capillary ridges.
Figure 15:
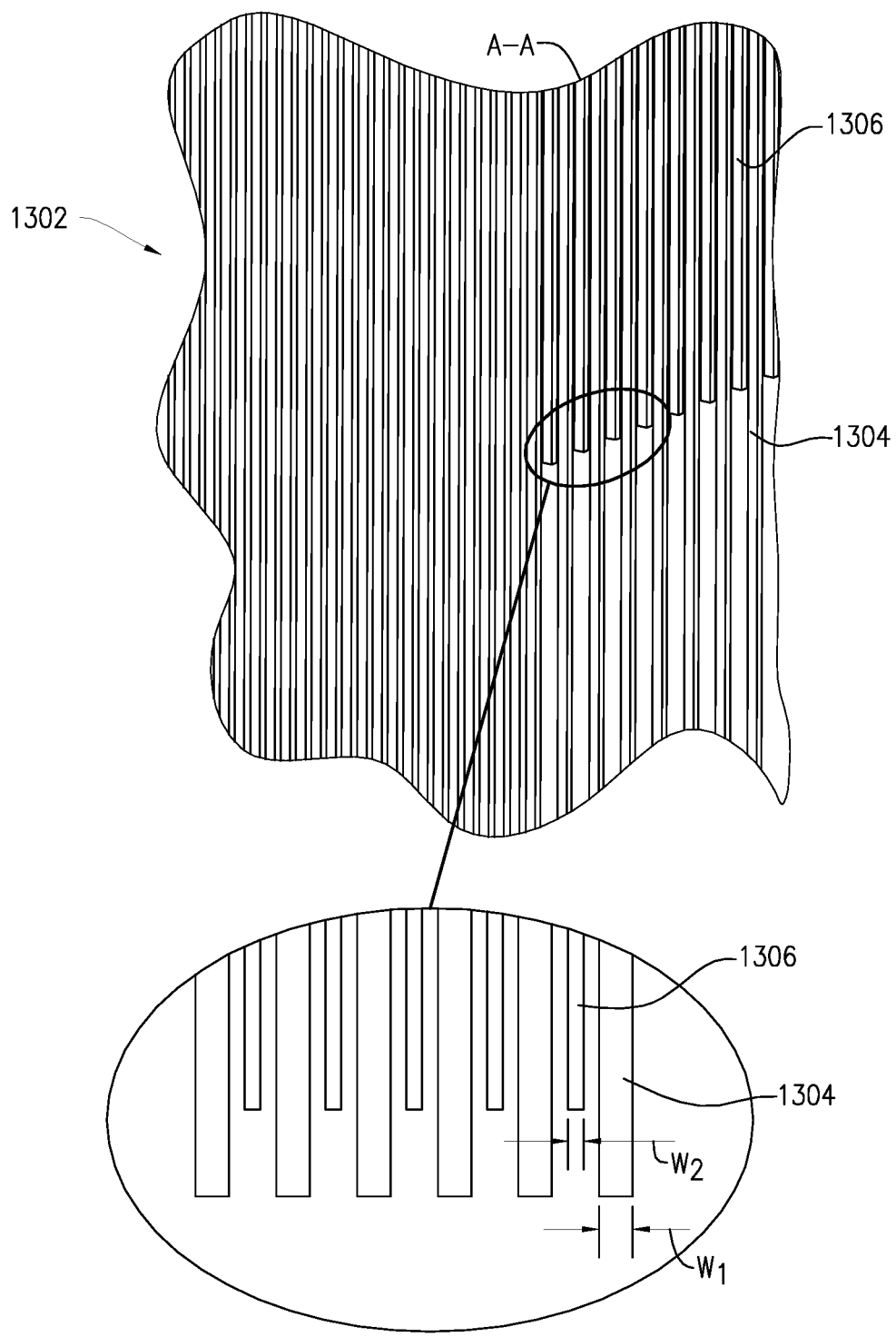
FIG. 15 is a close-up view a portion of the absorbent microstructure array of FIG. 14.

FIGS. 14 and 15 collectively illustrate yet another example absorbent microstructure array 1300 that comprises rows of capillary ridges of varying size and configuration. In one embodiment, the array 1300 is constructed from a plurality of microstructure panels such as microstructure panel 1302. A close up view of section A/A of the microstructure panel 1302 is illustrated in FIG. 15.

In one embodiment, the plurality of capillary ridges of the microstructure panel 1302 comprises two rows of capillary ridges. A first row 1304 of the two rows comprise capillary ridges having a first width $W_1$ and a second row 1306 of the two rows comprise capillary ridges create spaces with a second width $W_2$ that is different to that of the first width $W_1$. While two rows of capillary ridges are illustrated and described, additional rows of capillary ridges can be utilized. For example, a plurality of capillary ridges rows can be arranged such that the capillary channels (e.g., space between adjacent capillary ridges) of higher rows of capillary ridges are successively narrower towards a top of the microstructure array.

In some embodiments, the first row 1304 of the two rows of capillary ridges are offset from the second row 1306 of the two rows of capillary ridges such that the first row 1304 of the two rows of capillary ridges are disposed at least partially within in the spaces (capillary channels) between the second row 1306 of the two rows of capillary ridges. The interleaving or lacing of the first and second rows creates narrower spacing between the capillary ridges of the second row 1306 and adjacent capillary rows of the first row 1304 on either side of the narrower capillary ridges of the second row 1306.

Figure 16:
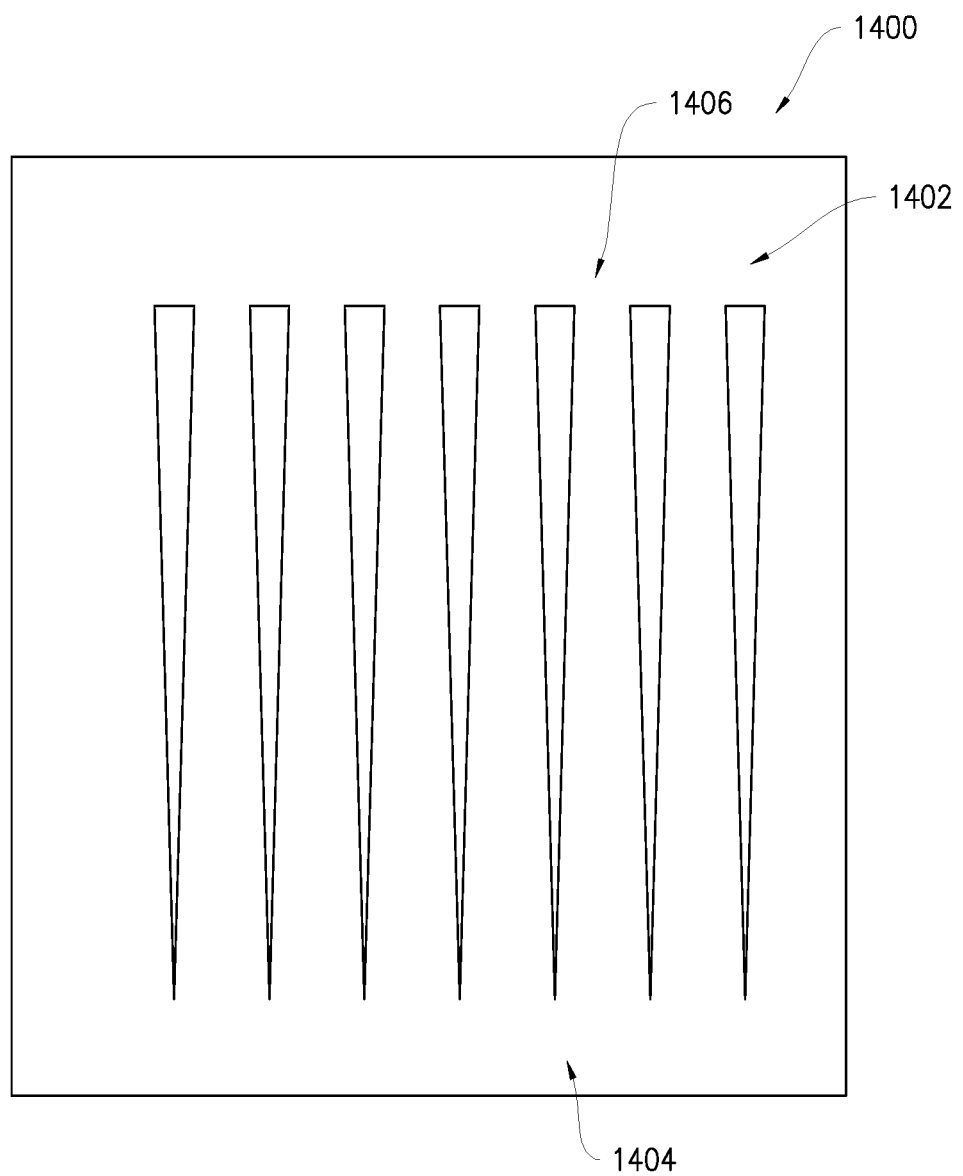
FIG. 16 is a perspective view of an example microstructure panel comprising tapered capillary ridges.

FIG. 16 illustrates a portion of another example microstructure panel 1400 that comprises a plurality of capillary ridges 1402 that are tapered from a lower edge 1404 to an upper edge 1406 to compensate for forces exerted on the fluid due to gravity. That is, as the space between adjacent capillary ridges narrows, the capillary effect increases, thereby increasing the velocity of the fluid to compensate for the force of gravity.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, device, assembly, sub-assembly, component, and combinations thereof. Alternatively, in some embodiments the "means for" is expressed in terms of prose, or as a flow chart or a diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "mechanically connected," etc., are used interchangeably herein to generally refer to the condition of being mechanically or physically connected. It is further noted that various figures (including component diagrams) shown and discussed herein are for illustrative purpose only, and are not drawn to scale.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. An absorbent microstructure array, comprising:
   a plurality of microstructure panels each having:
      a front surface, a back surface, and a first edge and a second edge, wherein the first edge and the second edge are opposite with respect to each other and wherein a third edge and a fourth edge are opposite with respect to each other; and a corrugated capillary profile associated with the front surface, the corrugated capillary profile comprises alternating arcuate capillary ridges and arcuate capillary channels, the alternating arcuate capillary ridges and the arcuate capillary channels being straight and extending orthogonally to the first edge and the second edge, the alternating arcuate capillary ridges forming a first set of capillary tubes with the front surface;

a capillary wall ridge disposed outside a periphery of the alternating arcuate capillary ridges, the capillary wall ridge comprising:

a first section extending parallel to a first outermost arcuate capillary ridge of the alternating arcuate capillary ridges;

a second section extending parallel to a second outermost arcuate capillary ridge of the alternating arcuate capillary ridges;

a third section extending orthogonally to first ends of the alternating arcuate capillary ridges, the third section being connected, by a first end of the third section, to the first section and connected, by a second end of the third section, to the second section; and one or more fourth sections extending from the third section along the alternating arcuate capillary ridges in a direction towards second ends of the alternating arcuate capillary ridges, the one or more fourth sections being disposed in parallel to the first section and the second section and being distributed uniformly between the first section and the second section, the one or more fourth sections segmenting the alternating arcuate capillary ridges into sections and restricting a fluid flow between the sections; and the plurality of microstructure panels form an absorbent microstructure array by layering the plurality of microstructure panels together such that the alternating arcuate capillary ridges of one microstructure panel contact the back surface of an adjacent microstructure panel to create a second set of capillary tubes from the arcuate capillary channels.

2. The absorbent microstructure array according to claim 1, wherein the plurality of microstructure panels are arranged at an angle relative to a reference plane P that is perpendicular to the plurality of microstructure panels when the plurality of microstructure panels are vertically oriented.

3. The absorbent microstructure array according to claim 2, further comprising a layer of enclosing microstructure panels that are placed over exposed ones of the plurality of capillary ridges of the plurality of microstructure panels, the layer of enclosing microstructure panels each having a flat front surface.

4. The absorbent microstructure array according to claim 1, further comprising an enclosing microstructure panel that is placed over the plurality of capillary ridges of a terminal microstructure panel of the plurality of microstructure panels, the enclosing microstructure panel having a flat front surface.

5. The absorbent microstructure array according to claim 1, wherein the capillary wall ridge connects to outermost capillary ridges and prevents fluid from being drawn above the capillary wall ridge.

6. The absorbent microstructure array according to claim 1, wherein at least a portion of the plurality of capillary ridges are tapered from the second edge to the first edge to compensate for forces exerted on fluid due to gravity.

7. The absorbent microstructure array according to claim 1, wherein the plurality of microstructure panels are constructed from a flexible material.

8. The absorbent microstructure array according to claim 1, wherein the plurality of capillary ridges and the front surface are coated with nano-structures that enhance capillary action of the plurality of microstructure panels relative to a plurality of microstructure panels with no nano-structure coating.

9. The absorbent microstructure array according to claim 1, wherein the plurality of capillary ridges comprise cross-cut notches.

10. The absorbent microstructure array according to claim 1, wherein the plurality of capillary ridges comprises two rows of capillary ridges, wherein a first of the two rows comprise capillary ridges having a first width and a second of the two rows comprise capillary ridges having a second width that is different that the first width.

11. The absorbent microstructure array according to claim 10, wherein the first of the two rows of capillary ridges is offset from the second of the two rows of capillary ridges such that the capillary ridges in the first of the two rows are disposed in the spaces between the capillary ridges of the second of the two rows of capillary ridges.

12. The absorbent microstructure array according to claim 10, wherein the capillary ridges of the first of the two rows of capillary ridges extend into the spaces between the capillary ridges of the second of the two rows of capillary ridges.

13. The absorbent microstructure array according to claim 1, wherein the plurality of capillary ridges extends from the first edge to the second edge of the microstructure panels.

* * * * *